United States Patent [19]

Takenaka et al.

[11] Patent Number: 4,990,530

[45] Date of Patent: Feb. 5, 1991

[54] INDOMETHACIN INJECTIONS AND THEIR PRODUCTION METHOD

[75] Inventors: Hiroshi Takenaka, Kyoto; Masatoshi Hasegawa, Takatsuki; Shu Matsuda, Ibaraki, all of Japan

[73] Assignee: Sumitomo Pharmaceuticals Company, Limited, Osaka, Japan

[21] Appl. No.: 388,474

[22] Filed: Aug. 2, 1989

[30] Foreign Application Priority Data

Aug. 8, 1988 [JP] Japan ................... 63-197627

[51] Int. Cl.⁵ ............................................. A61K 31/40
[52] U.S. Cl. ................................................... 514/420
[58] Field of Search ............................... 514/415, 420

[56] References Cited

U.S. PATENT DOCUMENTS 3,592,902  7/1971  Sato et al. ........................ 514/339
3,845,210 10/1974  Sato et al. ........................ 514/415

FOREIGN PATENT DOCUMENTS 0006223  1/1980  European Pat. Off. .
0237796  9/1987  European Pat. Off. .
1221506  2/1971  United Kingdom .

OTHER PUBLICATIONS

Abstract of Published Netherland Application NL86-02767, published May 16, 1988—Chem. Abstract #111:23101h (Gantax, S.A.).

Valone et al., J. Clin. Immunol., 4, 383–387 (1984).
Reddy et al., Int. J. Immunopharmacol., 7, 917–921 (1985).
Ramirez et al., Lancet, page 570, Sep. 6, 1986.
Greico et al., Int. J. Immunother., II(4), 295–300 (1986).
Zenk et al., Amer. J. Hosptl. Pharm., 43, 874, 878 (1986).
Meyler's Side Effects of Drugs, Ed., M. N. G. Dukes, vol. 8, 217–220, (1975).

*Primary Examiner*—Douglas W. Robinson
*Assistant Examiner*—Raymond J. Henley, III
*Attorney, Agent, or Firm*—Wenderoth, Lind & Ponack

[57] ABSTRACT

Injections containing anhydrous sodium indomethacin and methods for producing injections containing an hydrous sodium indomethacin which comprise converting a solution of indomethacin to a solution of sodium indomethacin by adding dropwise an aqueous solution of a carbonate of sodium, followed by freeze-drying and heating.

The injections of the present invention are practically useful indomethacin injections in which sodium indomethacin anhydride has high safety and chemically high purity and stability, and the lyophilized pharmaceutical preparations are excellent also in that redissolution thereof is facilitated. By the methods for the production of the present invention, it is possible to produce said anhydrous sodium indomethacin efficiently.

9 Claims, 3 Drawing Sheets

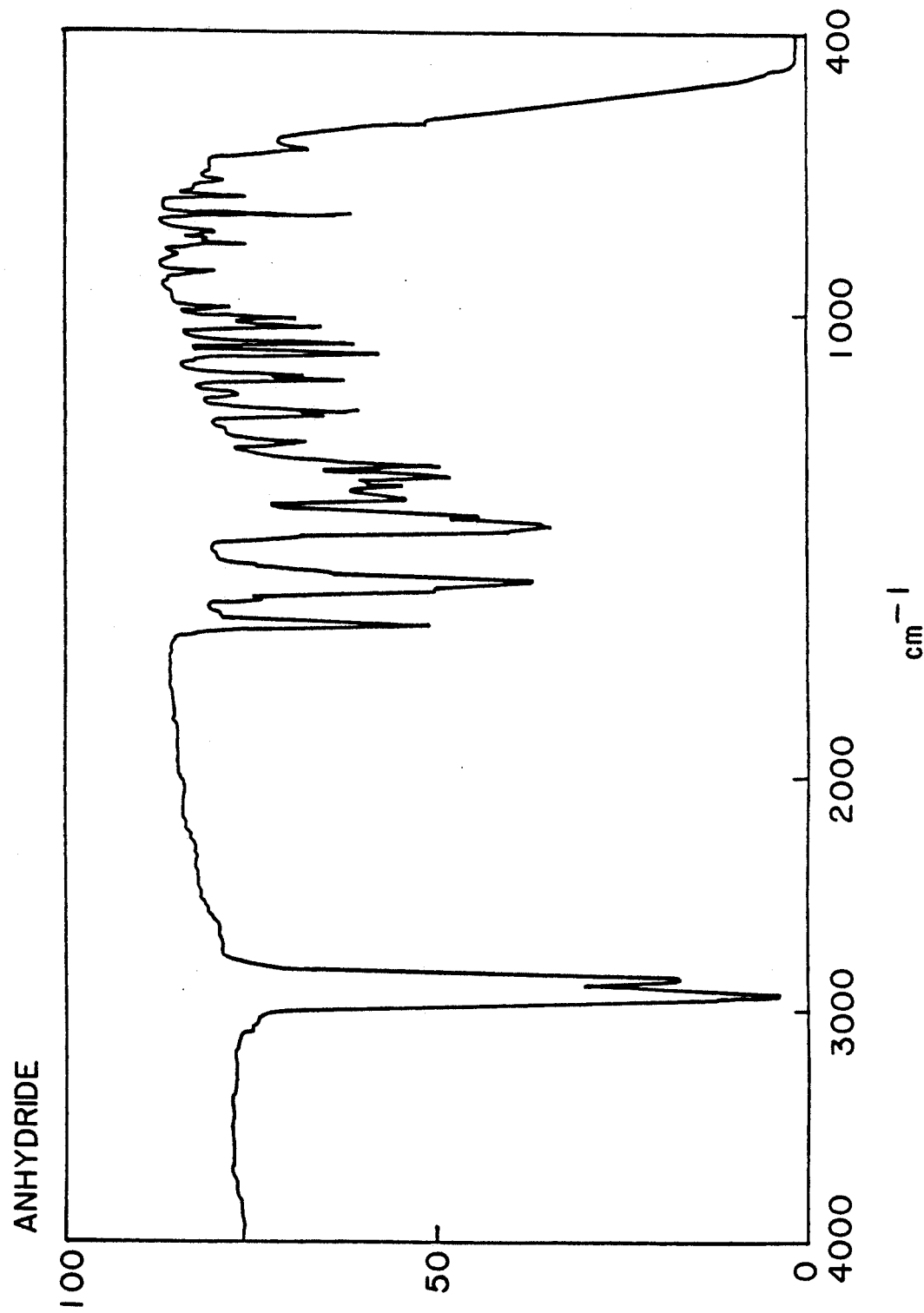
FIG. 1(a) ANHYDRIDE

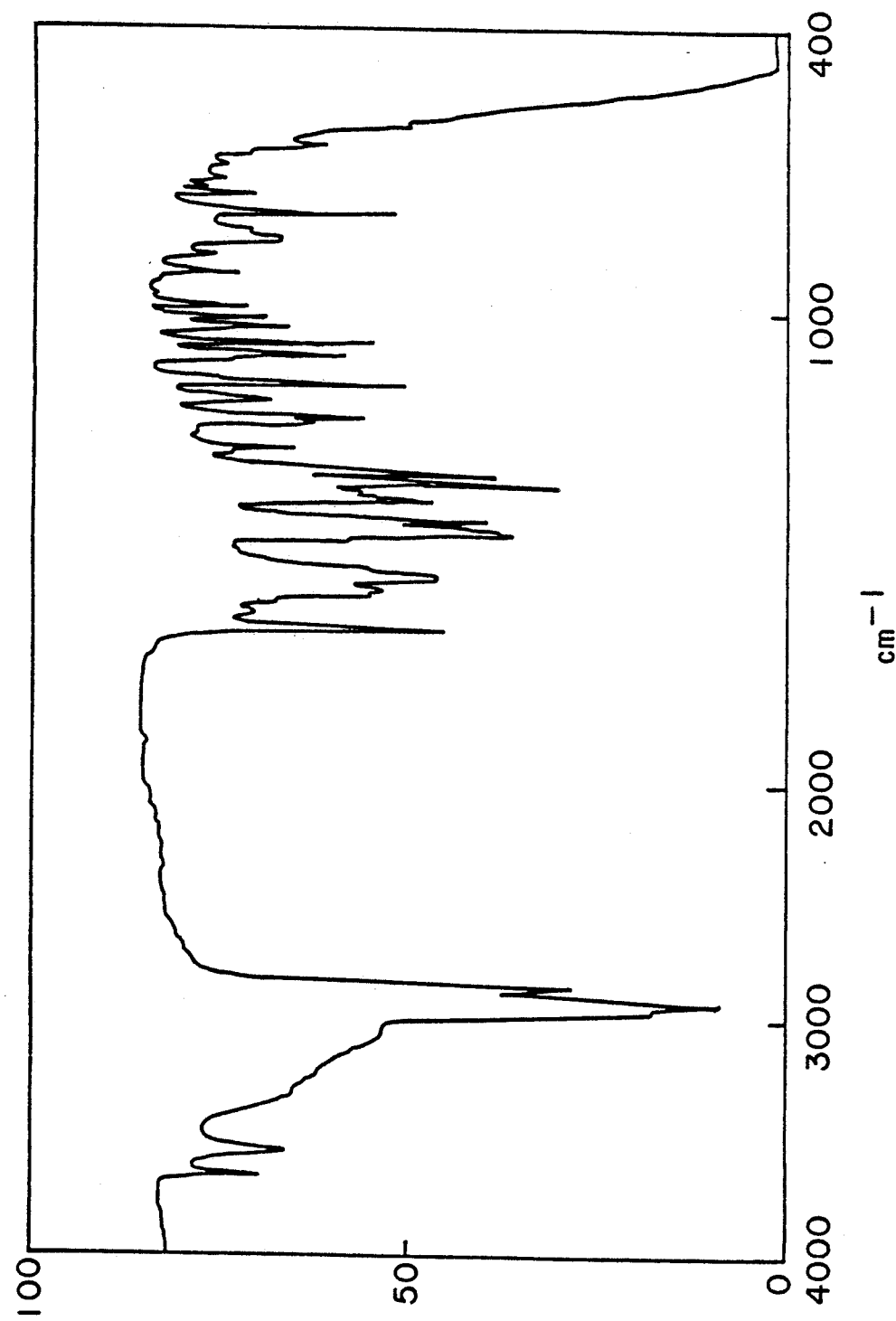
FIG. I (b)
TRIHYDRIDE

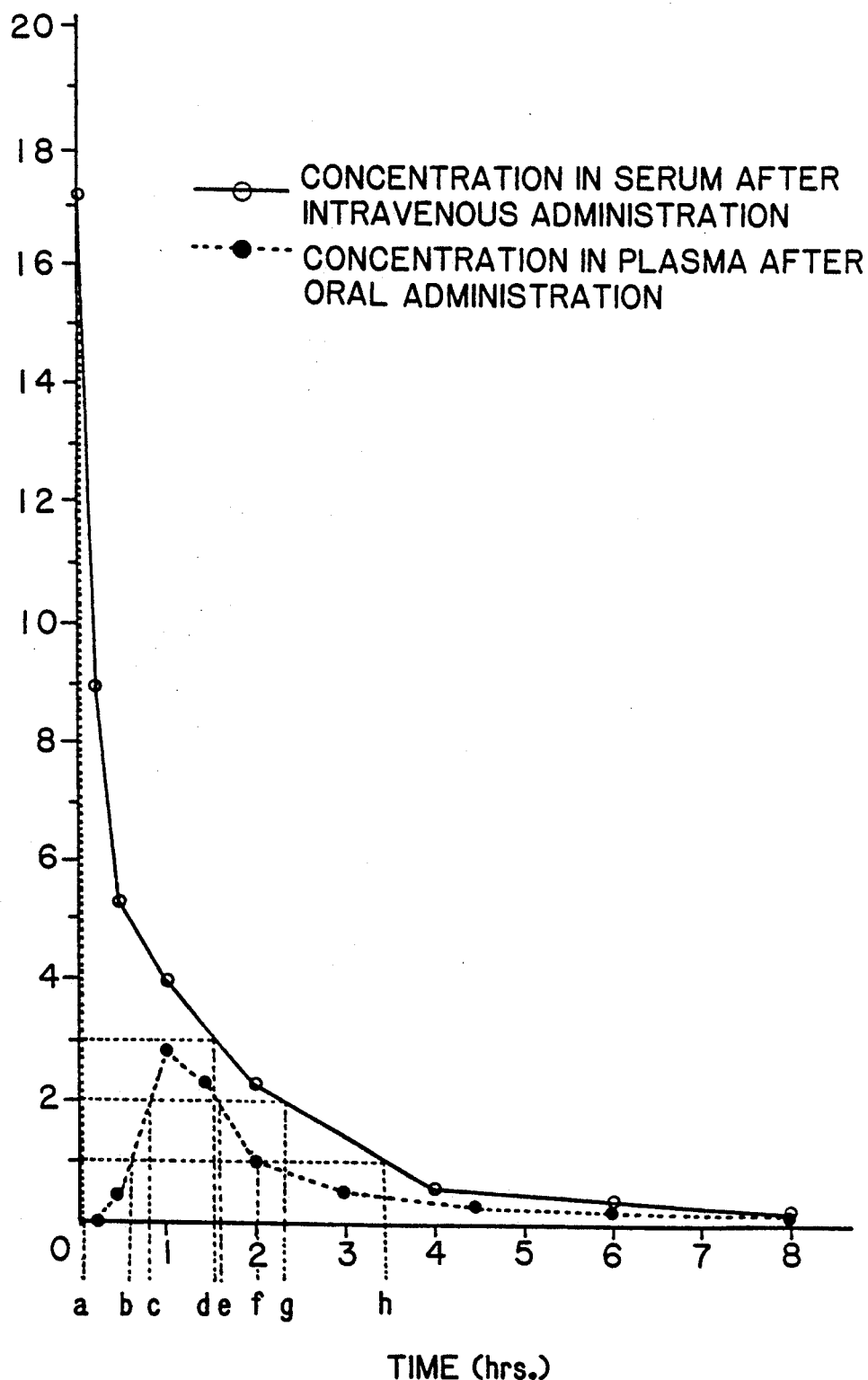

INDOMETHACIN INJECTIONS AND THEIR PRODUCTION METHOD

BACKGROUND OF THE INVENTION

This invention relates to practically useful injections of indomethacin and the methods for the production thereof. The injections of the present invention are useful for the therapy, prophylaxis or the like of, for example, acquired immune deficiency syndrome (AIDS) and AIDS related complex (ARC).

DESCRIPTION OF THE PRIOR ART

Indomethacin is a medicament which has heretofore been widely used as an antiinflammatory, antipyretic and analgesic in the clinical field, and also, the use thereof as a therapeutic agent for cancers has been attempted. In recent years, much attention has been paid to the use of it for the treatment of AIDS and ARC.

AIDS is a serious condition in which immunity is suppressed, which involves high mortality and is characterized by considerable deficiency of helper T cells. Most patients of AIDS result in death from opportunistic infection or cancer. This disease has become a socially important problem. Human Immunodeficiency Virus (HIV) has been isolated as novel retrovirus from AIDS patients, and the mutation of this virus is remarkable. It has been considered that CD4 lymphocyte which plays an important and main role in the immune system is the main host cell thereof. Though it is presumed that there exist other factors than HIV which are concerned in the mechanism causative of AIDS, there remains much to be clarified.

Recently, it has come to be suggested that indomethacin which is a cyclo-oxygenase-inhibitor and prostaglandin-synthesis-inhibitor can be used as a therapeutic agent for patients of AIDS and ARC, from an in vitro assessment with the use of lymphocytes of patients of AIDS and ARC [F. H. Valone et al, J. Clin. Immunol., 4, 383–387 (1984) and M. M. Reddy et al, Internal. J. Immunopharmacol., 7, 917–921 (1985)]. Furthermore, in vivo application or clinical application has been attempted. It has been shown that when indomethacin is orally administered to patients of AIDS or ARC, fever, languidness, anorexia and other clinical symptoms disappear or are improved, their body weight increase as well, and furthermore patients complicated by esophagus candidiasis can be cured of candidiasis without antifungal therapy [J. Ramirez et al, Lancet, Sep. 6, 570 (1986) and M. H. Grieco et al, Internal. J. Immunother., 11, 295–300 (1986)]. Among those patients, as far as those who retain immune function to some extent are concerned, their immune function can be recovered by oral administration of indomethacin. There is an invention in which the effectiveness on HIV of some prostaglandin-synthesis-inhibitors and cyclo-oxygenase-inhibitors have been confirmed based on in vitro evaluation, and these inhibitors have been made use of as treatment agents for AIDS (EP-A-237796). However, in this invention, it is not clear how effects on AIDS differ depending on the species of medicaments of the prostaglandin-synthesis-inhibitors, and the relationship between in vivo evaluation and clinical effects is not made clear.

It is absolutely essential for therapeutic medicines for AIDS and ARC to be efficiently delivered to the circulatory organ system in which the host cells of HIV exist. According to the report by Ramirez et al, when indomethacin was orally administered to AIDS patients at the dose of 75 mg every 8 hours for 4–8 weeks, its clinical effects was confirmed, and recovery of immune function was expected by continuance of the treatment with indomethacin for a longer period. However, while treatment by oral administration is generally desired, it is quite undesirable to administer a large amount of medicine over a long period from the view-point of safety. Besides, when indomethacin is orally administered, it is difficult to enable indomethacin at a safe dose to amount to a level of a concentration in blood sufficient enough to display its therapeutic effect as a treatment remedy for AIDS and ARC. By contrast, when indomethacin is administered by injection, it is possible to deliver it at the effective dose efficiently and safely to the circulatory system and further to the central nervous system accurately.

Accordingly, for the purpose of administering indomethacin more efficiently to the circulatory system and central nervous system, the development of injections has been strongly desired.

The production of indomethacin injections, however, involves many difficulties in the technological respect. Some of the problems are that indomethacin is a weak acidic substance of pKa of about 4, has low water-solubility and further, is subject to hydrolysis at the acyl group thereof by acid and base catalysts.

Though the production of its injections by lyophilization method is considered to be the effective means to solve the problems, an aqueous solution of soluble salts of indomethacin becomes incomplete in redissolution through physical procedures such as freezing procedure, and thus precipitation occurs in an aqueous solution of lyophylized product. Such incompleteness of redissolution can be improved by addition of a buffering agent containing inorganic ions as ingredient. However, when a buffering agent comprising inorganic ion is used, indomethacin is hydrolized by acid and base catalysts, thereby the acyl group is removed and, as the result, the pharmacological effect is reduced and besides, change in coloring occurs owing to the oxidative decomposition. Therefore, this buffering agent cannot be adopted.

In order to solve these problems, the present inventors have so far proposed a method for the production of stable injections of indomethacin which comprises using a basic amino acid as the solubilizing agent and dimethylacetamide or glycofurol as the nonaqueous solvent for injection (USP 3592902 (=GB 1195612)), a method for the production of stable indomethacin injections which can be well redissolved, which method comprises lyophilizing and adding organic amines such as ethylenediamine, alkanolamines, basic amino acids and the like which are usable for injections (GB 1221506) and so on.

These pharmaceutical preparations, however, have not been put into practical use because they have some problems with respect to side effects and safety mainly attributable to the additives used. Recently, an injection containing sodium indomethacin trihydrate, prepared by lyophilization method has been developed as a therapeutic agent for patient ductus arteriosus of prematurely delivered babies. This pharmaceutical preparation is susceptible to change in appearance, and change in color of the products from pale yellow to dark yellow has been pointed out [K. E. Zenk et al, Amer. J. Hosptl. Pharm. 43, 874–878 (1986)], and therefore the preparation is considered to be insufficient in respect of stability, quality and so on.

There has been reported an invention of crystalline sodium indomethacin, potassium indomethacin and their trihydrates as a water-soluble anti-inflammatory (EP-A-6223), but there is not given any description of anhydrous sodium indomethacin relating to the present invention.

It is indispensable that medicaments to be used for injections are free from being contaminated with impurities such as by-products, decomposed materials and the like, and have high purity.

Thus, the development of practically useful indomethacin injections which are free from the above-mentioned problems involves many difficulties to be overcome.

As mentioned above, considering social demand for therapeutic agents for AIDS and ARC, it is indeed strongly desired to develop practical indomethacin injections which are safe and chemically highly pure and stable, and are excellent in solubility in redissolution.

SUMMARY OF THE INVENTION

Thus, one of the objects of the present invention is to provide practical indomethacin injections which are highly safe, chemically highly pure and stable, and excellent in facility of redissolution as the lyophilized preparation.

Another object of the present invention is to provide an efficient method for producing said indomethacin injections having the aforementioned characteristic properties To attain the above-mentioned objects, the present inventors conducted intensive studies, which resulted in success in the production of novel anhydrous sodium indomethacin. Further studies on said compound by the present inventors showed that said anhydrous sodium indomethacin per se or injections containing said compound are chemically stable and free from problems such as change in coloring and the lyophilized pharmaceutical preparations excellently redissolve. Besides, the present inventors found that a method for producing injections containing anhydrous sodium indomethacin high purity efficiently under mild conditions and further confirmed the utility of said injections in humans, which culminated in the completion of the present invention.

That is, this invention relates to (1) injections containing anhydrous sodium indomethacin and (2) methods for producing injections containing anhydrous sodium indomethacin which comprises preparing an aqueous solution of sodium indomethacin by adding dropwise an aqueous solution of a carbonate of sodium to a solution of indomethacin, followed by lyophilization of the solution and heating.

BRIEF DESCRIPTION OF THE FIGURES

FIG. 1(a) and (b) show infrared absorption spectra of anhydrous sodium indomethacin and sodium indomethacin trihydrate respectively. FIG. 2 is a graph showing the results of change in concentration in serum of indomethacin measured with the lapse of time in the case of intravenous administration to human. The continuous line is for administration by the injections of the present invention and the dotted line is for the oral administration based on the data described in the report by Cooper et al [J. Chromatogr., 233, 289-296 (1982)].

DESCRIPTION OF THE INVENTION

Anhydrous sodium indomethacin in the pharmaceutical preparations of the present invention has water-content of not more than 4%, preferably not more than 2%, and is chemically anhydrous sodium indomethacin. By contrast, the stoichiometric water-content of sodium indomethacin trihydrate is 12.46%.

The injections of the present invention are usually stored in a sealed-pack substantially in the absence of water, and when applied, they are dissolved in an aqueous solvent for injections and used because said anhydrous sodium indomethacin is unstable to water. As said aqueous solvents to be used for dissolution for application, solvents known hitherto as such suffice. For example, injectable distilled water can be mentioned.

The injections of the present invention can be produced, for example, by the following method.

After indomethacin is dissolved in a safely acceptable solvent, preferably a water-soluble and volatile solvent (e.g. lower alcohols and lower ketones exemplified by methanol, ethanol, isopropanol, acetone and methyl ethyl ketone, particularly preferably ethanol), sodium indomethacin is obtained by adding dropwise an aqueous solution of a carbonate of sodium, followed, if necessary, by addition of an additive such as an appropriate excipient (e.g. sugars such as mannitol) and/or an isotonicing agent. By lyophilization followed by heating for obtaining sodium indomethacin in an anhydrous form, the injections can be produced. The heating is conducted usually at a temperature ranging from 10° C. to 60° C., preferably 20° C. to 40° C. after most part of water has been removed. Heating employed in the production method of the present invention is conducted for the purpose of further drying the obtained solution subsequent to freeze-drying.

As the carbonates of sodium, mention is made of, for example, sodium hydrogencarbonate and sodium carbonate. Particularly preferably, sodium hydrogencarbonate is used.

The reaction between indomethacin and a carbonate of sodium is preferably conducted under conditions as mild as possible in a short time particularly to avoid contamination of impurities such as by-products and decomposed materials. Usually, the reaction time ranges from about 5 to about 60 minutes and the reaction temperature ranges from about 10° C. to about 40° C. Sodium indomethacin can be prepared by adding dropwise an aqueous solution of a carbonate of sodium to a solution of indomethacin at such a rate that crystallization of indomethacin does not occur for the production of injections, the equivalent ratio of indomethacin relative to a carbonate of sodium is made 1-2, preferably 1-1.5 so that redissolution of the pharmaceutical preparation of lyophilized product may be facilitated and the active ingredient may be chemically stable.

In the injections of the present invention, the lower the water-content is, the more stable the anhydrous sodium indomethacin is. Also, it is preferable to be careful in the production and handling of the compound so that it may not be exposed to water atmosphere because it has strong hygroscopicity.

The injections of the present invention containing anhydrous sodium indomethacin can be used as therapeutic agents for AIDS, ARC, cancers, inflammatory and so on. While the dosage varies depending on symptom, body weight and the like, for example, for the treatment of AIDS, anhydrous sodium indomethacin is intramuscularly or intravenously administered at the dose corresponding to 25-200 mg of indomethacin every day or every, other day.

Anhydrous sodium indomethacin contained in the injections of the present invention produced in accordance with the methods of the present invention have so high purity that the content of impurity is not more than 1% (according to the analysis by liquid chromatography). Besides, the yield is almost quantitative, and it can be obtained in high yield. The injections and anhydrous sodium indomethacin are extremely chemically stable and excellent in facility of redissolution, and highly safe and therefore they are very practical.

As for sodium indomethacin trihydrate, there remains anxiety about its side-effects because its chemical stability is open to question and also it involves change in coloring, which makes itself unpractical. Thus, the present invention has enabled for the first time provision of practical indomethacin injections.

For example, when indomethacin is orally administered to humans at the dosage of 50 mg, according to known references, it is reported that the maximum concentration in plasma of indomethacin is about 1.4 $\mu$g/ml (according to the measurement by fluorophotometric method )[H. B. Hucker et al, J. Pharmacol. Exptl. Therap., 153, 237-249 (1966)] or about 3 $\mu$g/ml (according to the measurement by liquid chromatography method) [J. K. Cooper et al, J. Chromatogr., 233, 289-296 (1982)]. Though it is considered possible to enhance the concentration in blood thereof by orally administering indomethacin in a large amount, such administration in a large amount may cause display of serious side-effects such as digestive organ disorders. It is extremely difficult to enable the concentration in blood of indomethacin to amount to the sufficient level for the therapy of AIDS and ARC by oral administration at a safe dosage. When indomethacin is rectally administered to humans in the form of a suppository at the dose of 50 mg, the maximum concentration in plasma is reported to be about 1.3 $\mu$g/ml. In contrast thereto, when the injections containing anhydrous sodium indomethacin of the present invention in the amount corresponding to 50 mg of indomethacin are intravenously administered to humans, the concentration in serum of indomethacin at 2.5 minutes after the administration amounted to about 17 $\mu$g/ml (according to the measurement by liquid chromatography method), as shown in Test Example 3 mentioned below. The concentration in blood of indomethacin rises by the administration of the pharmaceutical preparations of the present invention as shown above, while there was not observed any side-effects such as headache, dizziness or stagger which are often observed in the case of oral administration of indomethacin. Therefore, the injections of the present invention are free of any problem in the aspect of safety, and can be administered at a large dosage. From these results, it is apparent that the injections of indomethacin have greater utility than oral preparations or suppositories thereof. Consequently, the indomethacin injections of the present invention are extremely useful medicaments as the therapeutic and preventive agents for AIDS and ARC, and further contributive in various other aspects.

By the present invention, it became possible for the first time to deliver indomethacin to the circulatory system and further to the central nervous system and the like efficiently at a higher concentration. It is considered that the injections of the present invention facilitate making appropriate administration schedules in accordance with the diagnosis by physicians of the pathema of AIDS and ARC, and thus greatly contribute to the therapy, prophylaxis and the like of AIDS and ARC.

Below, the present invention is described in more detail by illustrating working examples, and the effects of the present invention are shown by test examples. However, the present invention should not be construed as being limited to these examples.

EXAMPLE 1

| Indomethacin | 17.5 g |
|---|---|
| Sodium hydrogencarbonate | 6.2 g |
| Mannitol | 50 g | gencarbonate is 1:1.5.)

While a solution of said indomethacin in 150 ml of ethanol was stirred at room temperature (about 25° C.), a solution of said sodium hydrogencarbonate in 300 ml of injectable distilled water was added dropwise thereto over the period of about 10 minutes. The mixture was stirred for further 5 minutes for the completion of the reaction. This reaction mixture was diluted by adding a suitable amount of injectable distilled water, and said mannitol was added thereto and was dissolved therein. To the mixture were added 1 g of activated charcoal and injectable distilled water in such an amount that the total amount of the mixture was 1 l. The mixture was filtered. After this solution was preliminarily frozen at $-33°$ C. for 2 hours, the primary drying at 33° C. for 13 hours was conducted, followed by the secondary drying at 20° C. for 25 hours to produce a lyophilized injection containing anhydrous sodium indomethacin.

EXAMPLE 2

| Indomethacin | 16.7 g |
|---|---|
| Sodium hydrogencarbonate | 4.7 g |
| Mannitol | 50 g |

(The equivalent ratio of indomethacin to sodium hydrogencarbonate is 1:1.2.)

While a solution of said indomethacin in 150 ml of ethanol was stirred at room temperature (about 25° C.), a solution of said sodium hydrogencarbonate in 300 ml of injectable distilled water was added dropwise thereto over the period of about 10 minutes, followed by further 5 minutes' stirring for the completion of the reaction. Ethanol was almost distilled off under reduced pressure. The residue was diluted by addition of an appropriate amount of injectable distilled water, and said mannitol was added thereto and dissolved therein. To the mixture were added 1 g of activated charcoal and injectable distilled water in such an amount that the total amount was 1 l. The mixture was filtered. After the obtained solution was preliminarily frozen at $-33°$ C. for 2 hours, the primary drying at 0° C. for 2 hours was conducted, followed by the secondary drying at 20° C. for 6 hours, at 40° C. for 7 hours, at 25° C. for 11 hours and at 40° C. for 5 hours in order to produce a freeze-dried injection containing sodium indomethacin anhydride.

EXAMPLE 3

| Indomethacin | 16.7 g |
|---|---|

-continued

| Sodium hydrogencarbonate | 4.3 g |
|---|---|
| Mannitol | 50 g |

(The equivalent ratio of indomethacin to sodium hydrogencarbonate is 1:1.1.)

The procedure was conducted in the same manner as in Example 2, and the obtained filtrate was preliminarily frozen at −32° C. for 2 hours. Thereafter, the primary drying at −30° C. for 24 hours was conducted, followed by the secondary drying at 20° C. for 10 hours and at 40° C. for 5 hours in order to produce a freeze-dried injection containing sodium indomethacin anhydride.

EXAMPLE 4

| Indomethacin | 16.7 g |
|---|---|
| Sodium hydrogencarbonate | 4.7 g |

(The equivalent ratio of indomethacin to sodium hydrogencarbonate is 1:1.2.)

While a solution of said indomethacin in 150 ml of ethanol was stirred at room temperature (about 25° C.), a solution of said sodium hydrogencarbonate in 300 ml of injectable distilled water was added dropwise thereto over the period of about 10 minutes, followed by further 5 minutes' stirring for the completion of the reaction. Ethanol was almost distilled off under reduced pressure. Activated charcoal (1 g) was added to the residue, followed by addition of injectable distilled water in such an amount that the total amount was 1 l. The mixture was filtered. After the filtrate is preliminarily frozen at −32° C. for 2 hours, the primary drying at −30° C. for 21 hours was conducted, followed by the secondary drying at 20° C. for 17 hours and at 40° C. for 5 hours in order to produce a lyophilized injection containing anhydrous sodium indomethacin.

EXAMPLE 5

| Indomethacin | 50 g |
|---|---|
| Sodium hydrogencarbonate | 14 g |

(The equivalent ratio of indomethacin to sodium hydrogencarbonate is 1 : 1.2.)

While a solution of said indomethacin in 450 ml of ethanol was stirred at room temperature (about 25° C.), a solution of said sodium hydrogencarbonate in 150 ml of injectable distilled water was added dropwise thereto over the period of about 10 minutes, followed by 5 minutes' stirring for the completion of the reaction. Ethanol was distilled off under reduced pressure. Acetone (500 ml) was added to the residue to crystallize sodium indomethacin trihydrate. The crystals were filtered and dried under reduced pressure. The dried cake (8.9 g) was dissolved in 400 ml of injectable distilled water, and 0.5 g of activated charcoal was added to the solution and an injectable distilled water was added in such an amount that the total amount was 500 ml. The mixture was filtered. The filtrate was frozen and dried under the same conditions as in Example 4 to produce a lyophilized injection containing anhydrous sodium indomethacin.

TEXT EXAMPLE 1

As for the lyophilized pharmaceutical preparations of anhydrous sodium indomethacin produced in accordance with Examples 1-5, the water-content values measured according to Karl-Fischer's method are shown in Table 1. As apparent from the measured values, the water-content of even the highest water-containing preparation was 1.3% and the water-contents of most preparations were not more than 1%. Furthermore, infrared absorption spectra of anhydrous sodium indomethacin as produced in Example 4 and sodium indomethacin trihydrate as produced as the intermediate product in Example 5 (the sodium indomethacin collected by filtration was in a form of trihydrate) were measured, and the results are shown in FIG. 1. The measurement was conducted by paste method with the use of liquid paraffin. When these infrared absorption spectra were compared, it was noted that there was considerable difference between them in the absorption bands particularly in the vicinity of 3000–3700 cm$^{-1}$, which was attributable to water. That is, the spectra of the anhydrous sodium indomethacin in the pharmaceutical preparations of the present invention scarcely show this absorption band, whereas those of the trihydrate remarkably shows this absorption band. From the results of these tests, it was confirmed that the sodium indomethacin contained in the pharmaceutical preparations of the present invention were in anhydrous form.

TEST EXAMPLE 2

The lyophilized injections of anhydrous sodium indomethacin as produced in Examples 1-5 were stored at room temperature, and the residual contents were measured by liquid chromatography method. As a result, as shown in Table 2, no change was observed in the residual content of the indomethacin injections of the present invention even after they were stored for 1 year and thus, they were extremely stable, and no change in their appearance was observed either. Accordingly, it was confirmed that the indomethacin injections produced in accordance with the present invention were stable and practically useful injections.

The values in Table indicate the residual rate (%) of indomethacin in the preparations stored for each indicated period based on the content of indomethacin at the initial stage of the storage. Also, (-) in Table indicates that the appearance of the preparation was in the form of pale yellow powders in a bulky type.

TEST EXAMPLE 3

To the lyophilized preparation produced in Example 1 of the present invention containing anhydrous sodium indomethacin anhydride in the amount corresponding to 50 mg of indomethacin per vial was added 3 ml of injectable distilled water, to redissolve it. The total solution was intravenously administered to an adult man volunteer (at the age of 50) weighing 56 kg in the starting at 2.5 minutes' lapse after administration, the blood was collected from the veins in the left arm, and for each of the samples the concentration in serum of indomethacin was measured by liquid chromatography method.

The results are shown in FIG. 2. It was for the first time shown that at the 2.5 minutes' lapse after administration, the concentration in serum of indomethacin amounted to about 17 μg/ml. By comparing change in the concentration in blood after the intravenous administration shown herein with that after the oral administration at the same dose as reported by Cooper et al, it was found that by intravenous administration, the concentration in blood of not less than 3 μg/ml was retained for about 90 minutes (See a–d in FIG. 2), whereas by oral administration, the concentration in blood did not amount to this level. Moreover, the time during which the concentration in blood of not less than 2 μg/ml was retained was about 135 minutes in the case of intravenous administration (See a–g in FIG. 2) and about 45 minutes in the case of oral administration (See c–e in FIG. 2). The time during which a concentration in blood of not less than 1 μg/ml was about 200 minutes in the case of intravenous administration (See a–h in FIG. 2) and about 85 minutes in the case of oral administration (See b–f in FIG. 2). Besides, while the concentration in blood of indomethacin rose by intravenous administration as mentioned above, side-effects such as headache, dizziness or stagger were not observed at all.

From the foregoing results, the indomethacin injections of the present invention are considered extremely useful medicaments as the therapeutic agents for AIDS and ARC.

TABLE 1

| Pharmaceutical preparation | Water-content (%) |
| --- | --- |
| Example 1 | 1.3 |
| Example 2 | 0.3 |
| Example 3 | 0.7 |
| Example 4 | 0.9 |
| Example 5 | 1.3 |
| Trihydrate | 13.3 |

(Note) The stoichiometric water-content of trihydrate is 12.46% and the value in Table indicates the result obtained by measuring the water-content of sodium indomethacin trihydrate obtained as the intermediate product in Example 5.

TABLE 2

| Storage period (Month) | Example 1 | | Example 2 | | Example 3 | | Example 4 | | Example 5 | |
| --- | --- | --- | --- | --- | --- | --- | --- | --- | --- | --- |
| | Appearance | Evaluation | Appearance | Evaluation | Appearance | Evaluation | Appearance | Evaluation | Appearance | Evaluation |
| Initial | — | 100 | — | 100 | — | 100 | — | 100 | — | 100 |
| 1 | — | 100 | — | 101 | — | 100 | — | 99 | — | 99 |
| 3 | — | 101 | — | 100 | — | 101 | — | 99 | — | 100 |
| 6 | — | 101 | — | 99 | — | 100 | — | 100 | — | 102 |
| 12 | — | 99 | — | 100 | — | 99 | — | 100 | — | 101 |

We claim:

1. A method for producing an injectable substantially anhydrous sodium indomethacin composition, the water-content of which is not more than 4%, which consists essentially of converting a lower alkanol solution or a lower alkanone solution of indomethacin to a solution of sodium indomethacin by addition thereto of 1–2 equivalents of an aqueous solution of sodium hydrogen carbonate or an aqueous solution of sodium carbonate, and lyophilizing the thus-obtained solution to remove most of the water, followed by heating at 10° C. to 60° C.

2. The method as claimed in claim 1 wherein a lower alkanol solution is employed and said alkanol is methanol, ethanol or isopropyl alcohol.

3. The method as claimed in claim 1 wherein a lower alkanone solution is employed and said ketone is acetone or methyl ethyl ketone.

4. The method as claimed in any one of claims 1 to 3 wherein the amount of sodium hydrogen carbonate or sodium carbonate used is 1.0 to 1.5 equivalents.

5. The method as claimed in any one of claims 1 to 3 wherein an aqueous solution of sodium hydrogen carbonate is employed.

6. The method as claimed in any one of claims 1 to 3 wherein the heating temperature is in the range of from 20° C. to 40° C.

7. The method as claimed in any one of claims 1 to 3 wherein the water-content of the sodium indomethacin composition is not more than 2%.

8. The method as claimed in any one of claims 1 to 3 wherein the solution of sodium hydrogen carbonate or sodium carbonate is added dropwise.

9. The method as claimed in any one of claims 1 to 3 wherein said lyophilization is performed immediately after addition of said sodium hydrogen carbonate or sodium carbonate.

* * * * *